United States Patent
Kobayashi et al.

(10) Patent No.: US 9,867,596 B2
(45) Date of Patent: Jan. 16, 2018

(54) ULTRASONIC PROBE

(71) Applicant: HITACHI ALOKA MEDICAL, LTD., Mitaka-shi, Tokyo (JP)

(72) Inventors: Kazuhiro Kobayashi, Mitaka (JP); Toru Watanabe, Mitaka (JP)

(73) Assignee: Hitachi, Ltd., Tokyo (JP)

(*) Notice: Subject to any disclaimer, the term of this patent is extended or adjusted under 35 U.S.C. 154(b) by 139 days.

(21) Appl. No.: 14/438,699

(22) PCT Filed: Oct. 30, 2013

(86) PCT No.: PCT/JP2013/079348
§ 371 (c)(1),
(2) Date: Apr. 27, 2015

(87) PCT Pub. No.: WO2014/069499
PCT Pub. Date: May 8, 2014

(65) Prior Publication Data
US 2015/0289851 A1 Oct. 15, 2015

(30) Foreign Application Priority Data

Oct. 31, 2012 (JP) ................. 2012-240497

(51) Int. Cl.
*A61B 8/00* (2006.01)
*A61B 8/12* (2006.01)
*B06B 1/06* (2006.01)

(52) U.S. Cl.
CPC ............ *A61B 8/546* (2013.01); *A61B 8/12* (2013.01); *A61B 8/445* (2013.01); *A61B 8/4494* (2013.01);
(Continued)

(58) Field of Classification Search
CPC ............ A61B 8/445; A61B 8/12; A61B 8/546
See application file for complete search history.

(56) References Cited

U.S. PATENT DOCUMENTS 5,297,553 A 3/1994 Sliwa, Jr. et al.
6,039,694 A 3/2000 Larson et al.
(Continued)

FOREIGN PATENT DOCUMENTS

CN 102132586 A 7/2011
CN 102397085 A 4/2012
(Continued)

OTHER PUBLICATIONS

Mossesgeld. "Making Metal Origami from Sheet Metal", May 14, 2010. http://www.tomsguide.com/industrial-origami-metal-folding. news-6798. html.*
(Continued)

*Primary Examiner* — Long V Le
*Assistant Examiner* — Yi-Shan Yang
(74) *Attorney, Agent, or Firm* — Westerman, Hattori, Daniels & Adrian, LLP

(57) ABSTRACT

A body-cavity-insertion-type probe wherein an electronic circuit board is provided via a relay board on a back surface side of an oscillator unit. A backing member is joined to a center region of a back surface of the electronic circuit board. A wiring sheet is joined to a peripheral region of the back surface. A rear wing and a front wing of the wiring sheet surround a backing case, and a right wing and a left wing of an exhaust heat sheet protrude outward via two slits formed in a heat dissipation shell and are fixed on an outer surface of the heat dissipation shell. Heat generated by the electronic circuit board is transmitted to the heat dissipation shell via the exhaust heat sheet or the backing case, and heat is dissipated by the heat dissipation shell as a whole.

8 Claims, 13 Drawing Sheets

(52) U.S. Cl.
CPC ........ *B06B 1/0629* (2013.01); *B06B 2201/76* (2013.01)

(56) References Cited

U.S. PATENT DOCUMENTS

| | | | |
|---|---|---|---|
| 8,008,842 B2 | 8/2011 | Jiang et al. | |
| 8,382,673 B2* | 2/2013 | Nagano | A61B 8/00 600/459 |
| 2003/0028108 A1 | 2/2003 | Miller | |
| 2005/0046311 A1* | 3/2005 | Baumgartner | B06B 1/0292 310/334 |
| 2005/0075573 A1* | 4/2005 | Park | A61B 8/00 600/459 |
| 2005/0085731 A1 | 4/2005 | Miller et al. | |
| 2006/0043839 A1 | 3/2006 | Wildes et al. | |
| 2006/0058706 A1* | 3/2006 | Frey | B06B 1/0681 601/2 |
| 2009/0034370 A1* | 2/2009 | Guo | B06B 1/0622 367/180 |
| 2011/0152691 A1 | 6/2011 | Ikeda et al. | |
| 2012/0007471 A1* | 1/2012 | Tai | B06B 1/067 310/334 |
| 2012/0060610 A1 | 3/2012 | Oaks et al. | |
| 2014/0375171 A1 | 12/2014 | Tai | |

FOREIGN PATENT DOCUMENTS

| | | |
|---|---|---|
| JP | 10-75953 A | 3/1998 |
| JP | 2001-74710 A | 3/2001 |
| JP | 2005-507581 A | 3/2005 |
| JP | 2007-282743 A | 11/2007 |
| JP | 2011-229976 A | 11/2011 |
| WO | 03/013181 A2 | 2/2003 |
| WO | 2010/143387 A1 | 12/2010 |

OTHER PUBLICATIONS

V and F Sheet Metal. "FAQ—Sheet Metal Work", Oct. 1, 2011. http://www.vandf.co.uk/about/faq/.*
Notification of Transmittal of Copies of Translation of the International Preliminary Report on Patentabililty (Form PCT/IB/338) of International Application No. PCT/JP2013/079348 dated May 14, 2015 with Forms PCT/IB/373, PCT/IB/326 and PCT/ISA/237, with translation. (9 pages).
Office Action dated Apr. 29, 2016, issued in counterpart Chinese Patent Application No. 201380057153.3, with English translation (12 pages).
International Search Report dated Jan. 14, 2014, issued in corresponding application No. PCT/JP2013/079348.
Final Office Action dated Mar. 20, 2017, issued in U.S. Appl. No. 14/438,694 14 pages.
Sheet Metal Hand Brake Machines by Chicago Dries & Krump, American Machine Tools Co., May 22, 2012 (cited in final Office Action in US. Appl. No. 14/438,694).

* cited by examiner

ULTRASONIC PROBE

TECHNICAL FIELD

The present invention relates to an ultrasonic probe, and in particular, to a body cavity insertion type ultrasonic probe having a two-dimensional array transducer.

BACKGROUND ART

In the medical field, ultrasound diagnostic apparatuses are being used. An ultrasound diagnostic apparatus is a device that transmits and receives ultrasound to and from a living body, and forms an ultrasound image based on a reception signal obtained by the transmission and reception of the ultrasound. The transmission and reception of the ultrasound are executed by an ultrasonic probe. Various probes are commercialized, including a body cavity insertion type probe. The body cavity insertion type probe is inserted into the esophagus, the rectum, the vagina, or the like, and transmits and receives the ultrasound inside the body. Of these, the esophagus probe is a probe inserted into the esophagus, and more specifically, is a probe that transmits and receives ultrasound to and from the heart, while in the esophagus.

In recent years, three-dimensional ultrasound diagnosis is becoming more wide-spread. In this technique, ultrasound is transmitted and received to and from a three-dimensional space in a living body, to acquire volume data, and the volume data are used to form a three-dimensional image representing the three-dimensional space, a two-dimensional tomographic image representing an arbitrary cross section of the three-dimensional space, or the like. In order to transmit and receive the ultrasound to and from the three-dimensional space, in a probe head, in general, a two-dimensional array transducer is provided. The two-dimensional array transducer is formed by a plurality of transducer elements (for example, a few thousand transducer elements) arranged two-dimensionally.

Patent Document 1 discloses an esophagus probe for three-dimensional ultrasound diagnosis. A transducer unit is placed in the head of the esophagus probe. The transducer unit comprises a two-dimensional array transducer, an interface layer, an electronic circuit (integrated circuit), a backing layer, a heat sink, or the like, provided in that order from the side of a living tissue. The electronic circuit is a circuit that executes channel reduction; that is, a circuit for reducing the number of signal lines. The heat sink is a circuit that takes away heat generated in the electronic circuit.

RELATED ART REFERENCE

Patent Document

[Patent Document 1] JP 2005-507581 A

DISCLOSURE OF INVENTION

Technical Problem

When an electronic circuit for channel reduction is to be provided in the probe head, because a significant amount of heat is generated in the electronic circuit, heat dissipation from the electronic circuit becomes a problem. Specifically, when the heat generated in the electronic circuit is conducted to the two-dimensional array transducer, the temperature of the two-dimensional array transducer becomes high, resulting in a problem such as degradation of the two-dimensional array transducer and an increase in the temperature of the transmission/reception surface. In consideration of this, in order to avoid, as much as possible, conduction of the heat generated in the electronic circuit to the two-dimensional array transducer, it becomes necessary to discharge the heat from the electronic circuit to other members.

However, in the esophagus probe described in Patent Document 1, because the heat sink is provided on the back surface side of the electronic circuit with a backing layer therebetween, there is a problem in that it is difficult to increase the heat conduction efficiency from the electronic circuit to the heat sink. For this purpose, a configuration may be considered in which the backing layer is removed and the heat sink is joined directly to the electronic circuit. However, in such a structure, it is not possible to sufficiently attenuate the ultrasound emitted from the two-dimensional array transducer to the back surface side, resulting in a problem such as multiple reflection. In a body cavity insertion type probe, there is a strong demand for reducing the size of the probe head, and thus, it is not possible to provide a complex or large-size cooling mechanism in the probe head.

Solution to Problem

An advantage of the present invention is that, in an ultrasonic probe having an array transducer and an electronic circuit electrically connected to the array transducer, heat generated in the electronic circuit is effectively discharged and the temperature of the array transducer is prevented from becoming high. Another advantage of the present invention is that effective backing with respect to unnecessary ultrasound is realized at the back surface side of the array transducer, and heat generated in the electronic circuit is effectively discharged. Another advantage of the present invention is that, in a body insertion type probe, there is realized a probe head structure which can discharge the heat generated in the electronic circuit to the overall probe head.

According to one aspect of the present invention, there is provided an ultrasonic probe comprising: an array transducer having a plurality of transducer elements which are arranged two-dimensionally; an electronic circuit board provided on a side of a back surface of the array transducer and having an electronic circuit which is electrically connected to the plurality of transducer elements; and a heat dissipation member which is a heat conductive member joined to a heat conductive region on a back surface of the electronic circuit board and which discharges heat from the back surface side of the electronic circuit board to a heat discharge structure.

According to the above-described configuration, the heat dissipation member is joined directly to the heat conductive region which is set on the back surface of the electronic circuit board, and the heat moves from the back surface side of the electronic circuit board through the heat dissipation member to the heat discharge structure. With such a configuration, the heat generated in the electronic circuit board can be effectively discharged, and, consequently, heat conduction from the electronic circuit board to the array transducer can be inhibited and an excessive temperature increase in the array transducer can be prevented. Such a configuration allows improvements in the stability of the living body.

The electronic circuit described above forms at least one of a transmission signal processing circuit and a reception signal processing circuit, and preferably forms both processing circuits. The electronic circuit is preferably a channel reduction circuit. The channel reduction circuit generates, during transmission, a plurality of transmission drive signals from one transmission trigger signal by the array transducer as a whole or in a predetermined unit, and generates, during reception, one group reception signal from a plurality of reception signals in a predetermined unit. Preferably, the electronic circuit board is a semiconductor board on whose surface an electronic circuit is formed and that does not have a thick package. Such an electronic circuit board may be joined directly on the back surface side of the array transducer, but preferably, the electronic circuit board is connected to the array transducer with an interface board therebetween. As the interface board, there may be used a board which has a wiring converting function or the like. When the thermal conductivity of the heat dissipation member is higher than the thermal conductivity of the interface board, the heat generated in the electronic circuit can be more readily moved to the heat dissipation member. The array transducer is in general formed from a material having a piezoelectric characteristic, and a MUT (Micro-Machined Ultrasonic Transducer) may be used. Preferably, the heat discharge structure is a skeleton of the probe head and, at the same time, a heat discharge member, and more preferably, the heat discharge structure is a probe head case. With the use of a heat discharge structure formed with a member having a large surface area and superior thermal conductivity, it becomes possible to inhibit the temperature increase of the electronic circuit board while discharging the heat from the entirety of the heat discharge structure to the environment and without causing a local temperature increase. The ultrasonic probe is preferably a body cavity insertion type probe, and more preferably an esophagus probe.

According to another aspect of the present invention, preferably, the heat conductive region and an ultrasound propagation region are set on the back surface of the electronic circuit board, and the ultrasonic probe further comprises a backing member joined to the ultrasound propagation region. According to such a configuration, the heat dissipation function and the ultrasound attenuation function can be realized at the back surface side of the electronic circuit board. In other words, the inhibition of the temperature increase of the electronic circuit board and prevention of the multiple reflection can be realized simultaneously. According to another aspect of the present invention, preferably, the ultrasound propagation region is a center region, and the heat conductive region is an entirety of or a part of a peripheral region surrounding the center region. According to such a configuration, the backing function may be concentrated in the center region where the ultrasound tends to be more easily propagated, to effectively absorb the ultrasound. On the other hand, on the heat dissipation surface, the heat dissipation member is joined to the peripheral region. With such a structure also, a sufficient heat dissipation function may be achieved so long as the thermal conductivity of the electronic circuit board is not low; that is, so long as there is no temperature distribution that cannot be permitted. Preferably, the heat dissipation member is joined to the entirety of the peripheral region, but the heat dissipation member can be joined to a part of the peripheral region. In this case, preferably, there is employed a structure in which the heat dissipation member is joined to a portion, of the peripheral region, having high heat generation.

According to another aspect of the present invention, preferably, the heat dissipation member is a sheet-shaped member having an opening corresponding to the ultrasound propagation region, the backing member is a block-shaped member having a protrusion joined to the ultrasound propagation region through the opening, and the heat dissipation member is sandwiched between the electronic circuit board and the backing member. According to such a configuration, the protrusion of the backing member is joined directly to the center region on the back surface of the electronic circuit board through the opening of the heat dissipation member. On the other hand, the sheet-shaped heat dissipation member is surface-joined to the peripheral region on the back surface of the electronic circuit board. Because the heat dissipation member is sheet-shaped, the heat dissipation member can be easily deformed, and, consequently, it becomes easy to connect a larger part of the heat dissipation member to the heat conductive structure. According to another aspect of the present invention, preferably, the heat dissipation member comprises a plurality of wings extending from the heat conductive region and having flexibility, and at least one wing of the plurality of wings is joined to the heat discharge structure. According to such a configuration, at least one wing of the plurality of wings (portion widening in a planar shape) is joined to the heat conductive structure, and heat is discharged from the electronic circuit board with this structure. Preferably, all of the plurality of wings is joined directly or indirectly to the heat conductive structure.

According to another aspect of the present invention, preferably, at least one slit is formed on the heat discharge structure, the at least one wing is inserted to the at least one slit, and an inserted portion of the at least one wing is folded and joined to an outer surface of the heat discharge structure. According to such a configuration, the slit and the wing can be firmly connected, a superior heat conductive state can be achieved, and the heat dissipation member can be fixed on the heat discharge structure. According to the latter, because the heat dissipation member may function as a fixing member of an inner assembly, it becomes unnecessary to prepare a special member for the fixation, and the number of components can be reduced.

According to another aspect of the present invention, preferably, the ultrasonic probe further comprises a backing case that houses the backing member and that is formed by a heat conductive member, at least one wing of the plurality of wings is folded and joined to the backing case, and the backing case is joined to the heat discharge structure. According to such a configuration, superior heat conduction from the electronic circuit board to the heat discharge structure can be achieved, and the inner assembly can be held and fixed by the heat discharge structure through the backing case.

According to another aspect of the present invention, preferably, the heat dissipation member is a block-shaped member having an opening corresponding to the ultrasound propagation region, and the backing member is housed in the opening. According to such a configuration, a high heat absorption function can be achieved by the block-shaped heat dissipation member while securing a certain degree of backing function.

According to another aspect of the present invention, preferably, the heat discharge structure is formed by a heat conductive container that houses an inner assembly including the array transducer and the electronic circuit board. According to another aspect of the present invention, preferably, the heat conductive container is a probe head case that defines an outer shape of a probe head. According to another aspect of the present invention, preferably, the electronic circuit board is a semiconductor board on a surface of which the electronic circuit is formed. For example, the semiconductor board is a board that does not have a package and that is coated with a thin protection film.

EMBODIMENT

A preferred embodiment of the present invention will now be described with reference to the drawings.

Figure 1:
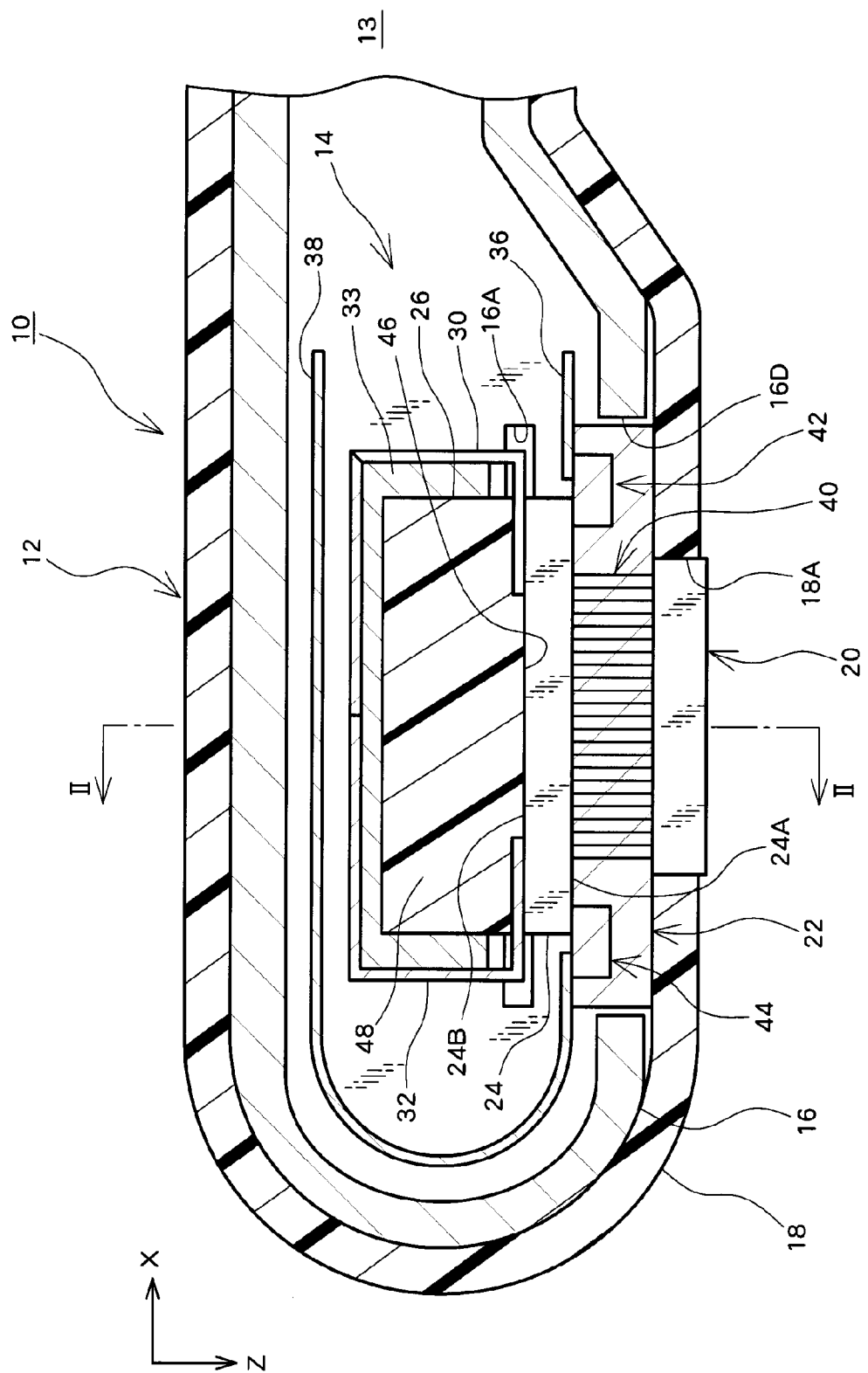
FIG. 1 is an XZ cross sectional diagram showing a preferred embodiment of a body cavity insertion type probe according to the present invention.

FIG. 1 shows an ultrasonic probe of a preferred embodiment according to the present invention. FIG. 1 is a cross sectional diagram (XZ cross sectional diagram) of the ultrasonic probe. The ultrasonic probe is a body cavity insertion type probe, and, in particular, an esophagus probe.

In FIG. 1, a probe 10 comprises a probe head 12, an insertion tube 13, an operation unit, a probe cable, etc. In the present embodiment, the probe head 12 is a portion that is inserted into the esophagus in the living body and that transmits and receives ultrasound while in the esophagus. During the ultrasound diagnosis, the probe head 12 is positioned in the esophagus such that a site to be diagnosed in a heart is included in a three-dimensional space which is an ultrasound transmission/reception region.

The inside of the probe head 12 is hollow, and an inner assembly 14 is placed therein. Alternatively, a filler material such as a resin may be filled around the inner assembly 14. The inner assembly 14 transmits and receives ultrasound in a Z direction; that is, a downward direction in FIG. 1. An X direction is a central axis direction of the probe head 12, the Z direction is the transmission/reception direction, and a Y direction is defined as a direction orthogonal to the X direction and the Z direction. The inner assembly 14 is more specifically placed inside a heat discharge shell 16. The heat discharge shell 16 is a hard, hollow container formed by a heat conductive member such as copper, and forms a probe head case. In other words, the heat discharge shell 16 forms an outer skeleton or a structure in the probe head 12. On an outer side of the heat discharge shell 16, an outer skin 18 is provided which is relatively soft and which is formed from a resin or the like having an insulating characteristic. On a side of the living body tissue of the heat discharge shell 16, an opening 16D is formed, and a part of the inner assembly 14 protrudes to the outer side of the heat discharge shell 16 through the opening 16D. The inner assembly 14 comprises a transducer unit 20, an interface board 22, an electronic circuit board 24, a backing member 26, a heat dissipation sheet having a plurality of wings, a backing case 33, etc., as will be described below. These members will be described below in detail.

As will be described later with reference to FIG. 4, the array transducer is formed by a plurality of transducer elements arranged along the X direction and the Y direction, and more specifically, is formed by a few thousand transducer elements. An ultrasound beam is formed by the array transducer and is electrically scanned. As the method of electrical scanning, an electron sector scanning method or the like is known. In the present embodiment, the ultrasound beam can be two-dimensionally scanned, and, with such a scan, a three-dimensional space is formed. A three-dimensional ultrasound image or the like representing the three-dimensional space can be formed by processing volume data acquired from the three-dimensional space. As shown in FIG. 1, on the side of the living body of the outer skin 18, an opening 18A is formed, and a part of the transducer unit 20 on the living body side expands and extends from the opening 18A to the living body side. In the execution of the ultrasound diagnosis, a state is created in which a surface of the transducer unit 20 on the living body side; that is, the transmission/reception surface, is in close contact with the inner surface of the esophagus which is a living body tissue surface.

On the back surface side of the transducer unit 20; that is, the upper side in FIG. 1, the interface board 22 is provided. The interface board 22 has a function to electrically connect the array transducer and an electronic circuit formed on the electronic circuit board 24. In the present embodiment, the interface board 22 is formed by a multilayer board, and has a lead array 40. The lead array 40 consists of a plurality of signal lines that electrically connect between the plurality of transducer elements and a plurality of terminals on the electronic circuit. The interface board 22 may alternatively be an interposer having an arrangement conversion function. That is, the electrode arrangement on the side of the array transducer and the electrode arrangement on the side of the electronic circuit may differ from each other. In the present embodiment, the interface board 22 also has a function to connect flexible boards 36 and 38 to be described below and the electronic circuit, and, for this purpose, groups of connection lines 42 and 44 are provided in the interface board 22. As shown in FIG. 1, the interface board 22 is placed in the opening 16D formed in the heat discharge shell 16. The basic material of the interface board 22 is, for example, ceramic having an insulating characteristic.

On the back surface side of the interface board 22; that is, the upper side in FIG. 1, the electronic circuit board 24 is provided. The electronic circuit board 24 has an electronic circuit for channel reduction. Specifically, the electronic circuit generates, during transmission, a plurality of transmission drive signals based on a transmission trigger signal transmitted from a side of a device body for the array transducer as a whole or in a predetermined unit, and supplies the transmission drive signals to the array transducer. During reception, the electronic circuit executes a phased summing process for a plurality of reception signals in units of element group, and generates a group reception signal. By providing such a channel reduction circuit, it is possible to significantly reduce the number of signal lines connected to the probe head. For example, the signals for all transducer elements, which are provided in a few thousand in number, can be processed by connecting only about 100 signal lines. In the present embodiment, the electronic circuit board 24 is formed by a substantially exposed semiconductor board on a surface of which the electronic circuit is formed. In other words, a package functioning as an outer cover is not provided, and the entirety of the semiconductor board is protected by a thin protection layer. On a surface 24A of the electronic circuit board 24 on the living body side, a plurality of electrodes corresponding to the plurality of transducer elements are formed. The lead array 40 described above is connected to the plurality of electrodes. A thickness of the electronic circuit board 24 in the Z direction is, for example, about 0.6 mm. A thickness of the above-described interface board 22 in the Z direction is, for example, about 1 mm.

On a back surface 24B of the electronic circuit board 24, there are set an ultrasound propagation region which is a center region and a heat dissipation region which is a peripheral region. The backing member 26 is joined to the ultrasound propagation region. More specifically, the backing member 26 is formed by a block-shaped body 48 and a protrusion 46 formed on the living body side of the body 48, and a surface of the protrusion 46 on the living body side is joined to the ultrasound propagation region. The heat dissipation sheet is joined to the peripheral region, as will be described later in detail. More specifically, the heat dissipation sheet has an opening, the protrusion 46 is joined to the center part on the back surface side of the electronic circuit board 24 through the opening, and, with such a configuration, the heat dissipation sheet is sandwiched between the body 48 of the backing member 26 and the heat dissipation region which is the peripheral region of the electronic circuit board 24. The heat dissipation sheet has a rear wing 30 and a front wing 32 shown in FIG. 1. In addition, the heat dissipation sheet also has a right wing and a left wing, which are not shown in FIG. 1. The backing member 26 scatters and attenuates unnecessary ultrasound emitted to the back surface side. For example, the backing member 26 has an acoustic attenuation characteristic of about 6~15 dB/cmMHz.

The backing member is formed, for example, by mixing tungsten, a tungsten compound, or the like into a resin. In this case, as the resin, there may be exemplified a thermoplastic resin such as nylon, polyethylene, polypropylene, polystyrene, or the like; a thermosetting resin such as an epoxy resin, a phenol resin, a urea resin, a melanin resin, or the like; and various rubbers. In manufacturing the backing member, in order to realize a desired acoustic impedance and a desired acoustic attenuation characteristic, a suitable amount of powder of tungsten, the tungsten compound, or the like is mixed into the resin. Alternatively, other materials may be mixed.

The heat dissipation sheet described above is formed, for example, from a carbon sheet, a graphite sheet, a sheet made of a metal such as copper, or the like, and is formed from a material having superior thermal conductivity. A thickness of the backing member 26 in the Z direction is, for example, about 3 mm.

Figure 2:
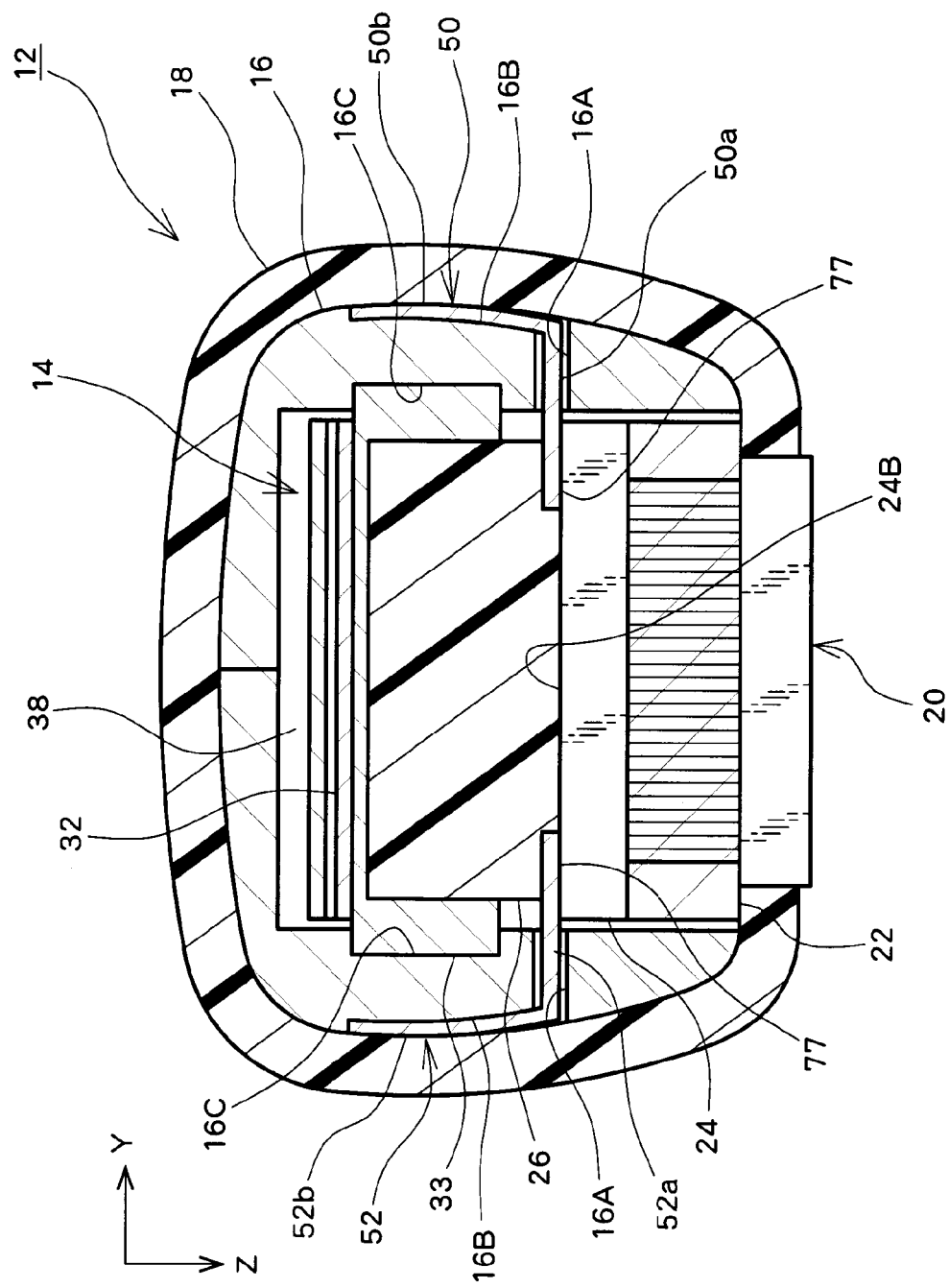
FIG. 2 is a YZ cross sectional diagram of the probe shown in FIG. 1.

The backing member 26 is surrounded by the backing case 33 except for the end on the living body side. That is, the body 48 of the backing member 26 is housed in the backing case 33. The backing case 33 functions as a heat conductive member and a jig. In the present embodiment, the rear wing 30 and the front wing 32 in the heat dissipation sheet are folded in a manner to extend along the outer surface of the backing case 33, and are adhered on the outer surface of the backing case 33. Therefore, the heat moves from the back surface side of the electronic circuit board 24 to the backing case 33 through the rear wing 30 and the front wing 32. As shown in FIG. 2 described below, the backing case 33 is joined and fixed to the heat discharge shell 16, and heat conduction occurs from the backing case 33 to the heat discharge shell 16. In addition, the heat discharge shell 16 holds and fixes the backing case 33 in the probe head 12. In addition to the above, heat is conducted from the back surface side of the electronic circuit board 24 to the heat discharge shell 16 through the right wing and the left wing of the heat dissipation sheet, as will be described below in detail.

On the ends on the back surface side of the interface board 22; that is, a non-living body side, flexible boards 36 and 38 are connected. Each of the flexible boards 36 and 38 is formed from an FPC (flexible printed circuit board), and has a wiring pattern. A plurality of signal lines are connected to the ends of the flexible boards 36 and 38 on the side of the device body. However, these signal lines are not shown in FIG. 1. Alternatively, the plurality of signal lines may be connected to the flexible boards 36 and 38 by means of a connector. As shown in FIG. 2, in the heat discharge shell 16, a slit 16A is formed on each of the side surfaces on both sides in the Y direction. The right wing and the left wing to be described later are inserted into the two slits 16A. In the present embodiment, the flexible board 38 is provided in addition to the flexible board 36, in order to reliably connect a large number of signal lines. As shown in FIG. 1, the flexible board 38 extends from a tip edge on the interface board 22 to the upper part, passes on the back surface side of the inner assembly 14; that is, the upper part in FIG. 1, and extends toward the body of the ultrasound diagnostic apparatus. Alternatively, the flexible board 38 may be omitted so long as the connection of the plurality of signal lines can be reliably achieved.

FIG. 2 shows a cross section in a direction shown by II in FIG. 1; that is, the YZ cross section. As already described, the probe head 12 has the heat discharge shell 16. The heat discharge shell 16 functions as a heat conductive structure; that is, a heat discharge structure, and also as a probe head case. The heat discharge shell 16 is covered by the outer skin 18. The inner assembly 14 is provided inside the probe head 12, and comprises the transducer unit 20, the interface board 22, the electronic circuit board 24, the backing member 26, and the backing case 33, provided in that order from the living body side. The heat dissipation sheet is sandwiched between the electronic circuit board 24 and the backing member 26. The heat dissipation sheet includes a body portion 77 serving as a heat reception portion, and a plurality of wings connected thereto. The plurality of wings more specifically include the rear wing and the front wing described above, and the right wing 50 and the left wing 52 shown in FIG. 2. The right wing 50 and the left wing 52 are inserted into a pair of the slits 16A formed on right and left side walls of the heat discharge shell 16. Each slit 16A is a through channel extending along the X direction. The body portion 77 in the heat dissipation sheet is a portion sandwiched between the electronic circuit board 24 and the backing member 26, and a front surface of the body portion 77 is joined to the peripheral region on the back surface of the electronic circuit board 24. The right wing 50 and the left wing 52 have first portions 50a and 52a connected to the body portions 77 and passing through the slits 16A, and second portions 50b and 52b connected to the first portions 50a and 52a and serving as an extension which extends vertically upward. The second portions 50b and 52b are folded and adhered on the outer surface of the heat discharge shell 16. More specifically, a pair of recesses 16B are formed on the outer wall surface of the heat discharge shell 16, and the pair of the second portions 50b and 52b are housed and fixed inside the recesses 16B. Therefore, the heat generated in the electronic circuit board 24 is conducted directly to the outer surface of the heat discharge shell 16 through the right wing 50 and the left wing 52. A depth of the recess 16B corresponds to a thickness obtained by adding a thickness of each of the wings 50 and 52 and a thickness of the adhesive. In a state where the second portions 50b and 52b are housed in the recesses 16B, a flat-surface state is formed. Alternatively, during the adhesion of the members, in order to achieve a superior thermal conductivity, there may be used an adhesive in which a heat conductive filler is mixed. Alternatively, grease having a heat conductive characteristic may be applied on the joining surface.

A pair of depressions 16C are formed on both sides in the Y direction on the inner surface of the heat discharge shell 16, and the ends of the backing case 33 are inserted into the depressions 16C. In other words, the backing case 33 is held and fixed by the heat discharge shell 16. Because the backing case 33 is fixed by the heat discharge shell 16 and the right wing 50 and the left wing 52 are fixed with respect to the heat discharge shell 16, the inner assembly 14 is reliably fixed to the heat discharge shell 16. As described above, the heat dissipation sheet has the rear wing 30 and the front wing 32, which are joined and fixed to the backing case 33. This structure also contributes to the fixation action of the inner assembly 14.

Figure 3:
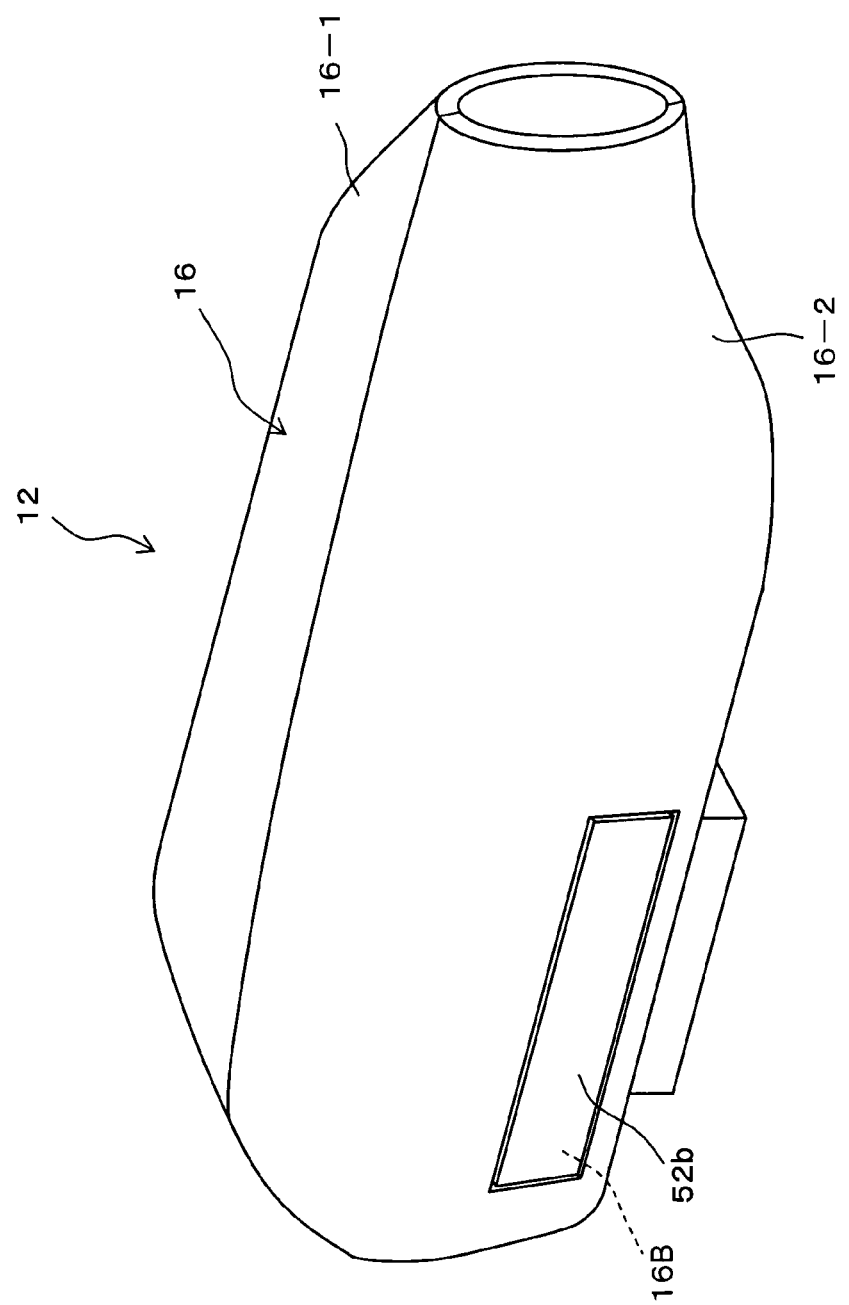
FIG. 3 is a perspective diagram showing a heat discharge shell forming a probe head case.

FIG. 3 is a perspective diagram of the heat discharge shell 16 described above. The heat discharge shell 16 is divided into 2 parts in the left-and-right direction, and is formed from a right side portion 16-1 and a left side portion 16-2. As described above, the slits 16A are formed on the right side surface and the left side surface of the heat discharge shell 16, the right wing and the left wing are inserted into the respective slits 16A, and the right and left wings are fixed in a folded state. In FIG. 3, the second portion 52b of the left wing is shown. As shown in FIG. 3, the heat discharge shell 16 forms a structure as an outer skeleton, and has a very large surface area. Therefore, when the heat generated in the electronic circuit is conducted to the heat discharge shell 16, the heat discharge shell 16 as a whole can effectively discharge the heat to the outside environment. The outside environment in this case includes the periphery of the probe head through the outer skin, and also the insertion tube and the large number of signal lines or the like passing inside the insertion tube. With such a configuration, the generated heat can be absorbed with the large member while avoiding a local temperature increase, and, by discharging the absorbed heat through the large area, the temperature increase in the electronic circuit board can be effectively inhibited, and, consequently, the temperature increase of the array transducer and the transmission/reception surface can be effectively inhibited. In particular, in the present embodiment, the heat discharge shell 16 functions as a fixing member of the inner assembly 14; that is, the connection structure for fixation can be used as the heat dissipation structure, and, thus, an advantage can be obtained also from the viewpoint of the number of components.

Figure 4:
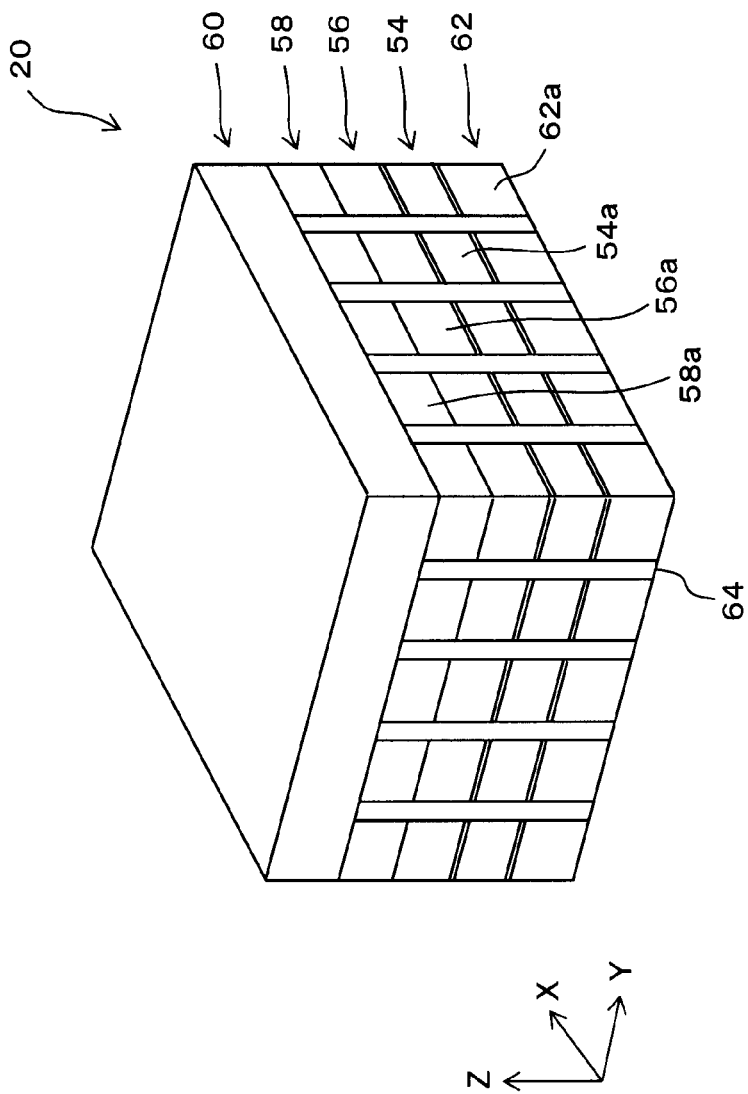
FIG. 4 is a diagram showing an example of a transducer unit.

FIG. 4 shows a specific example of the transducer unit 20 shown in FIG. 1. In FIG. 4, an upper part on the page is the living body side. The array transducer 54 is formed from a plurality of transducer elements 54a arranged along the X direction and the Y direction. The array transducer 54 is formed from a material such as, for example, PZT (piezoelectric zirconate titanate), quartz, zinc oxide, or the like, or is formed from a composite material including such a piezoelectric material. The array transducer may also be formed by MUT. The thickness of the individual transducer element 54a in the Z direction is set to around ¼λ with reference to a center frequency of the ultrasound.

A resonance layer 62 having a conductive characteristic is provided on the back surface side of the array transducer 54. The resonance layer 62 is formed by a plurality of resonance elements 62a arranged along the X direction and the Y direction. The resonance layer 62 assists the transmission and reception of the ultrasound at the array transducer 54. The resonance layer 62 is formed from a material having a conductive characteristic, and is formed, for example, as a composite structure including cobalt, zirconia, a tungsten compound, or the like. The materials described in the present specification are merely exemplary. An acoustic impedance in the array transducer 54 is, for example, about 30 MRayls, and the acoustic impedance of the resonance layer 62 is, for example, about 70~100 MRayls. In other words, in the present embodiment, the resonance layer 62 forms a hard backing layer, and the array transducer 54 and the resonance layer 62 together transmit and receive the ultrasound. The resonance layer 62 also has an electrical connection function between the array transducer 54 and the interface board. A thin metal foil forming an electrode is provided on an upper surface and a lower surface of each transducer element 54a, and is formed from, for example, gold, silver, etc.

For reference, the acoustic impedances of the members on the back surface side of the array transducer 54 will be described. The acoustic impedance of the interface board shown in FIG. 1 or the like is, for example, about 19 MRayls, and the acoustic impedance of the electronic circuit board is, for example, about 17 MRayls. In other words, the interface board and the electronic circuit board have approximately the same acoustic impedance, and reflection of the ultrasound at the boundary surface of these boards is prevented as much as possible. The acoustic impedance of the backing member is, for example, about 15~25 MRayls, and, with such a setting, the reflection of the ultrasound at the boundary surface between the electronic circuit board and the backing member is prevented to the extent possible. With such a configuration, the ultrasound exiting from the back surface side of the array transducer and the conductive resonance layer naturally reaches the backing member through the interface board and the electronic circuit board, and unnecessary ultrasound exiting to the back surface side is effectively attenuated and absorbed by the backing member. Even if reflection is generated at the back surface of the backing member 26, the reflected wave is also effectively attenuated and absorbed in the backing member. Therefore, the problem of the multiple reflection caused between the transmission/reception surface and the back surface of the backing member can be effectively prevented in cases, for example, in which the ultrasonic probe is left in the air. During the normal ultrasound diagnosis also, the unnecessary ultrasound exiting to the back surface side can be effectively absorbed, to improve image quality.

Referring again to FIG. 4, a first matching layer 56 and a second matching layer 58 are provided on the living body side of the array transducer 54. The first matching layer 56 is formed from a plurality of matching elements 56a which are two-dimensionally arranged, and the second matching layer 58 is formed from a plurality of matching elements 58a which are two-dimensionally arranged. A protection layer 60 is provided on the living body side of the second matching layer 58. The living body side surface forms the transmission/reception surface. Reference numeral 64 shows a separation channel formed between adjacent elements. The separation channel 64 may be an air layer, but in the present embodiment, silicone rubber or the like having acoustic insulating characteristic is filled in the separation channel 64.

Figure 5:
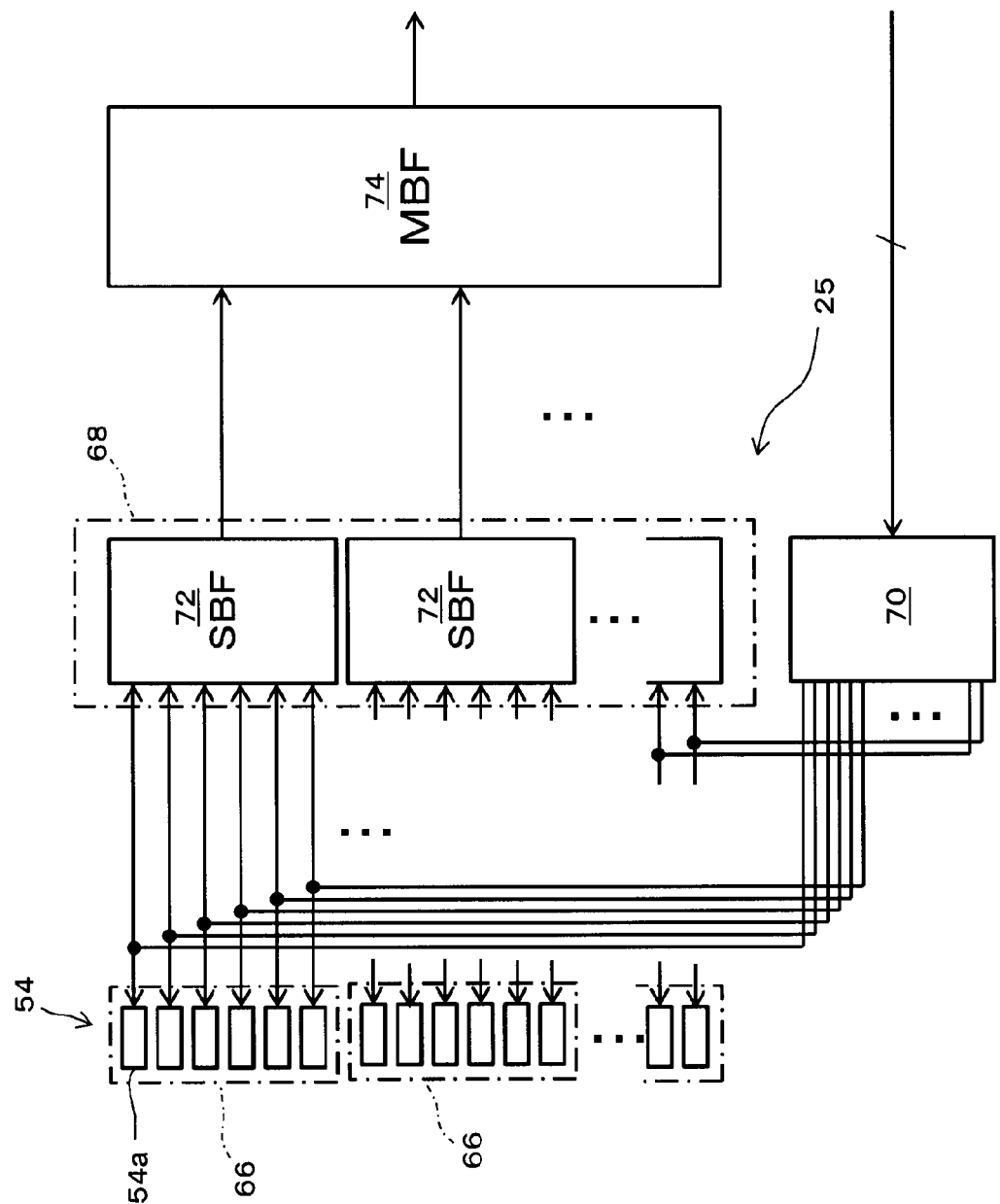
FIG. 5 is a diagram showing an example structure of a transmission and reception circuit.

FIG. 5 shows an example configuration of an electronic circuit 25 of the electronic circuit board. As described above, the array transducer 54 is formed by a plurality of transducer elements 54*a* which are arranged two-dimensionally. In the present embodiment, a plurality of groups 66 are set for the array transducer 54, and each group 66 is formed from a plurality of transducer elements that are grouped in a predetermined shape. The electronic circuit 25 is formed by a transmission signal processing circuit 70 and a reception signal processing circuit 68. The transmission signal processing circuit 70 generates a plurality of transmission drive signals to be supplied to the plurality of transducer elements based on a transmission control signal (including a transmission trigger signal) from the device body side. One transmission signal processing circuit 70 may be provided for the entirety of the array transducer 54 or the transmission signal processing circuit 70 may be provided for each group 66. In either case, the transmission signal processing circuit 70 generates a plurality of transmission drive signals from one transmission control signal, and realizes a process corresponding to the channel reduction during transmission.

The reception signal processing circuit 68 is formed from a plurality of sub beam formers (SBF) 72 corresponding to the plurality of groups 66 in the present embodiment. Each SBF 72 executes a phased summing process (sub phased summing process) for the plurality of reception signals output from the corresponding group 66, to generate a group reception signal after phased summing. With such a process, a plurality of group reception signals are generated, a main phased summing process is executed at a main beam former (MBF) 74 on the group reception signals, and phase-alignment beam data corresponding to the reception beam are generated. Here, the MBF 74 is provided in the device body. Each SBF 72 executes the channel reduction during reception. In the present embodiment, for example, phased summing process is executed for 16 reception signals, to generate one group reception signal.

As heat is generated in the process of executing the transmission/reception signal processes, unless the heat dissipation process is effectively executed, the temperature of the electronic circuit board would be increased and the temperatures of the array transducer and the transmission/reception surface would also be consequently increased. On the other hand, in the present embodiment, with the above-described heat dissipation process; that is, with a process to conduct heat from the electronic circuit board to the heat discharge shell through the heat dissipation sheet (and the backing case), and with a process to discharge heat over the entirety of the heat discharge shell, it is possible to effectively discharge the heat generated in the electronic circuit board to the outside.

Next, an example operation of the probe shown in FIG. 1 or the like will be described. The probe head 12 shown in FIG. 1 is inserted from a mouth to the esophagus of a subject, and the probe head 12 is positioned at a predetermined position in the esophagus. With this process, the transmission/reception surface of the probe head 12 is set to be in close contact with the inner wall surface of the esophagus. By transmitting and receiving the ultrasound in this state; more specifically, by executing a two-dimensional scan of the ultrasound beam, a three-dimensional region including a measurement site in the heart is formed, and volume data corresponding to the three-dimensional region can be acquired. Based on such volume data, an ultrasound three-dimensional image representing the three-dimensional space is formed, or there is formed an arbitrary tomographic image representing an arbitrary cross section in the three-dimensional space or a tri-plane image representing a plurality of predetermined cross sections.

More specifically, during transmission, a transmission signal is supplied from the device body side through the cable to the probe head 12. The transmission signal is sent through the flexible board 36 or the flexible board 38, and the interface board 22, to the electronic circuit. The transmission signal processing circuit in the electronic circuit generates a plurality of transmission drive signals based on the single transmission signal, and supplies the plurality of signals to the plurality of corresponding transducer elements. In this case, the plurality of transmission drive signals are sent to the array transducer through the lead array formed on the interface board as described above. With the supply of the plurality of the transmission drive signals, a transmission beam is formed in the array transducer. In this process, if unnecessary ultrasound is emitted to the back surface side of the array transducer, the unnecessary ultrasound is effectively absorbed and reduced by the backing member 26.

On the other hand, during the reception, when a reflected wave from the inside of the living body is received by the array transducer, a plurality of reception signals are sent from the array transducer to the electronic circuit through the lead array 40 on the interface board 22. In the reception signal processing unit of the electronic circuit, a sub phased-summing process is executed for the plurality of reception signals in units of each group, to generate group reception signals. A plurality of group reception signals generated in this manner are transmitted to the plurality of signal lines through the flexible board 36 and the flexible board 38, and further to the device body. In the device body, the main phased-summing process is executed based on the plurality of group reception signals, to generate beam data corresponding to the reception beam. During the reception, even if the reflected wave appears on the back surface side of the array transducer, such unnecessary ultrasound is effectively reduced by the backing member 26.

Next, thermal action will be described. The heat generated at the electronic circuit by the transmission/reception signal processes or the like is conducted to the heat discharge shell 16 through the heat dissipation sheet joined on the back surface side of the electronic circuit board 24. Specifically, the heat conducted to the rear wing 30 and the front wing 32 of the heat dissipation sheet is conducted through the backing case 33 to the heat discharge shell 16. On the other hand, the heat conducted to the right wing and the left wing of the heat dissipation sheet is directly conducted to the outer surface of the heat discharge shell 16. In this manner, the heat can be effectively conducted to the heat discharge shell 16 through 4 wings. Because the heat discharge shell 16 is formed as a member having a very large thermal capacity and having a very large surface area, the conducted heat can be effectively discharged to the outside, and local heat generation can be prevented.

In the present embodiment, the thermal conductivity of the electronic circuit board 24 and the heat dissipation sheet is set higher than the thermal conductivity of the interface board 22, and thus, a large part of the heat generated in the electronic circuit board is conducted to the heat dissipation sheet. In other words, the interface board has a certain heat separation function, and even if there is heat conduction by the lead array 40, heat conduction to the array transducer through the interface board 22 is inhibited.

In the present embodiment, as described above, the backing member 26 is joined on the center part on the back surface of the electronic circuit board 24, and the heat dissipation sheet is joined at the peripheral region on the back surface. With such a configuration, the backing function provided by the backing member can be applied to a part where the propagation of the ultrasound tends to occur more easily, to effectively absorb the unnecessary ultrasound. On the other hand, in the peripheral region, heat conduction similar to that in the center region occurs, and heat can be effectively taken away from the peripheral region through the heat dissipation sheet. In other words, on the back surface side of the electronic circuit board, both absorption of the unnecessary ultrasound and heat dissipation for inhibiting heat generation can be realized. In particular, in the above-described embodiment, the backing member 26 is housed in the backing case 33, and the backing case 33 is surrounded by the rear wing 30 and the front wing 32. Thus, an outer skeleton can be constructed around the backing member 26 which is in general soft, and the entirety of the inner assembly 14 can be fixed by holding the backing member 26. As a result, firm holding of the inner assembly 14 on the living body side becomes not necessary. Alternatively, other fixation methods may be used for holding the inner assembly 14 as necessary.

Next, a manufacturing method of the probe shown in FIG. 1 will be described with reference to FIGS. 6~11.

Figure 6:
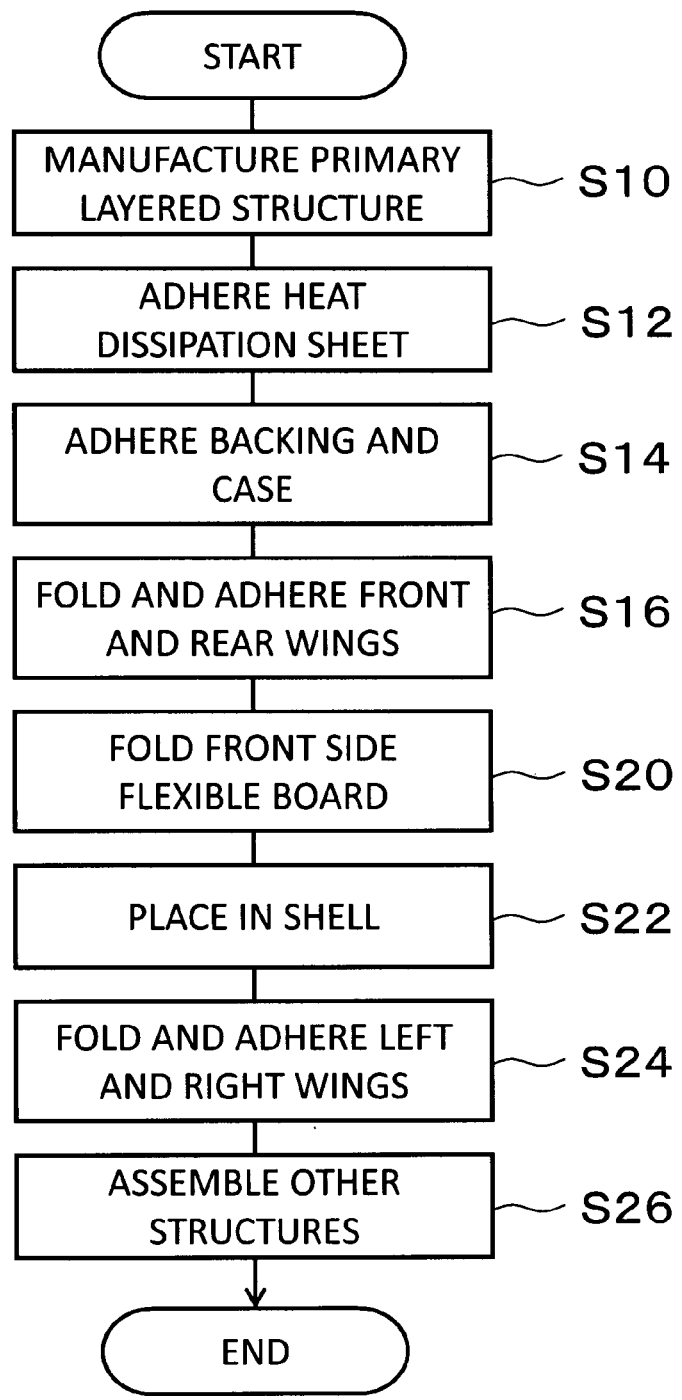
FIG. 6 is a flowchart showing an example method of manufacturing a probe according to a preferred embodiment of the present invention.
Figure 7:
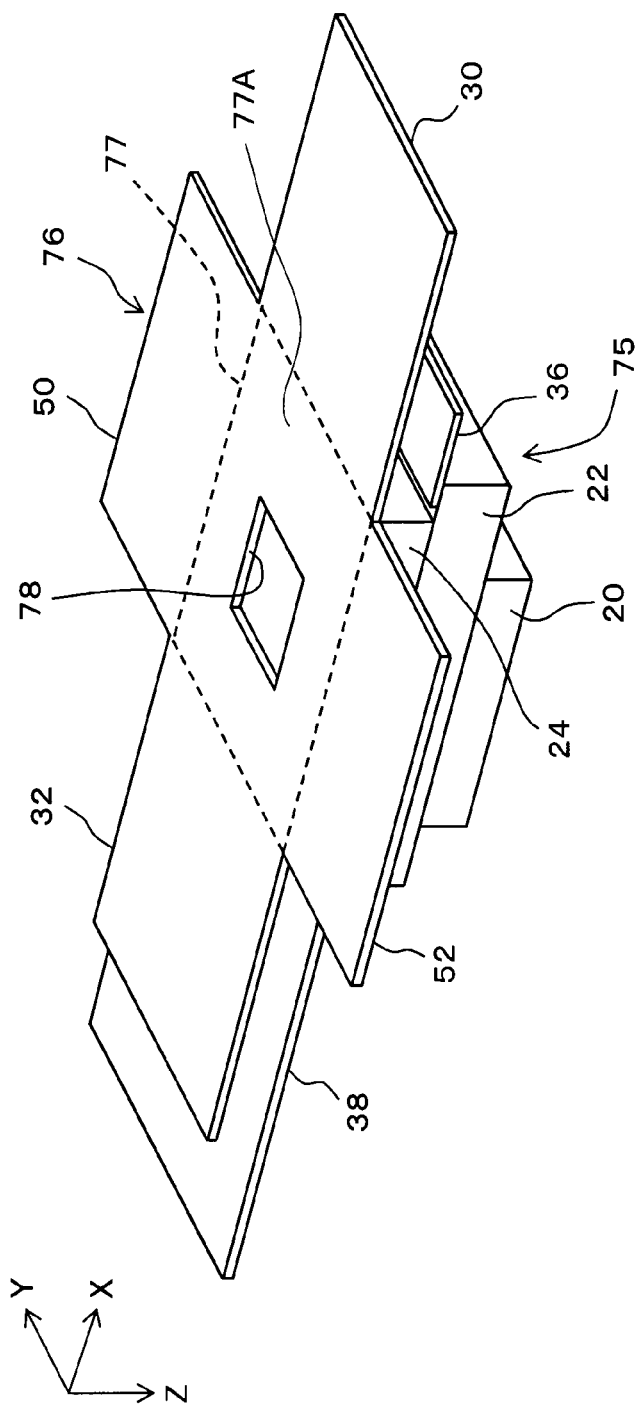
FIG. 7 is a diagram for explaining adhesion of a heat dissipation sheet to a primary layered structure.

In S10 in FIG. 6, a primary layered structure 75 shown in FIG. 7 is manufactured. That is, the primary layered structure 75 including the transducer unit 20, the interface board 22, and the electronic circuit board 24 is formed. The flexible boards 36 and 38 are attached to the interface board 22.

In S12 of FIG. 6, as shown in FIG. 7, a heat dissipation sheet 76 is adhered onto the primary layered structure 75. The heat dissipation sheet 76 includes the body portion 77 having an opening 78, and a plurality of wings connected thereto. The plurality of wings include the rear wing 30 and the front wing 32 arranged along the X direction, and the right wing 50 and the left wing 52 arranged along the Y direction. Reference numeral 77A shows an area corresponding to the peripheral region on the back surface of the electronic circuit board 24. The form of the heat dissipation sheet 76 is not limited to that shown in FIG. 7.

Figure 8:
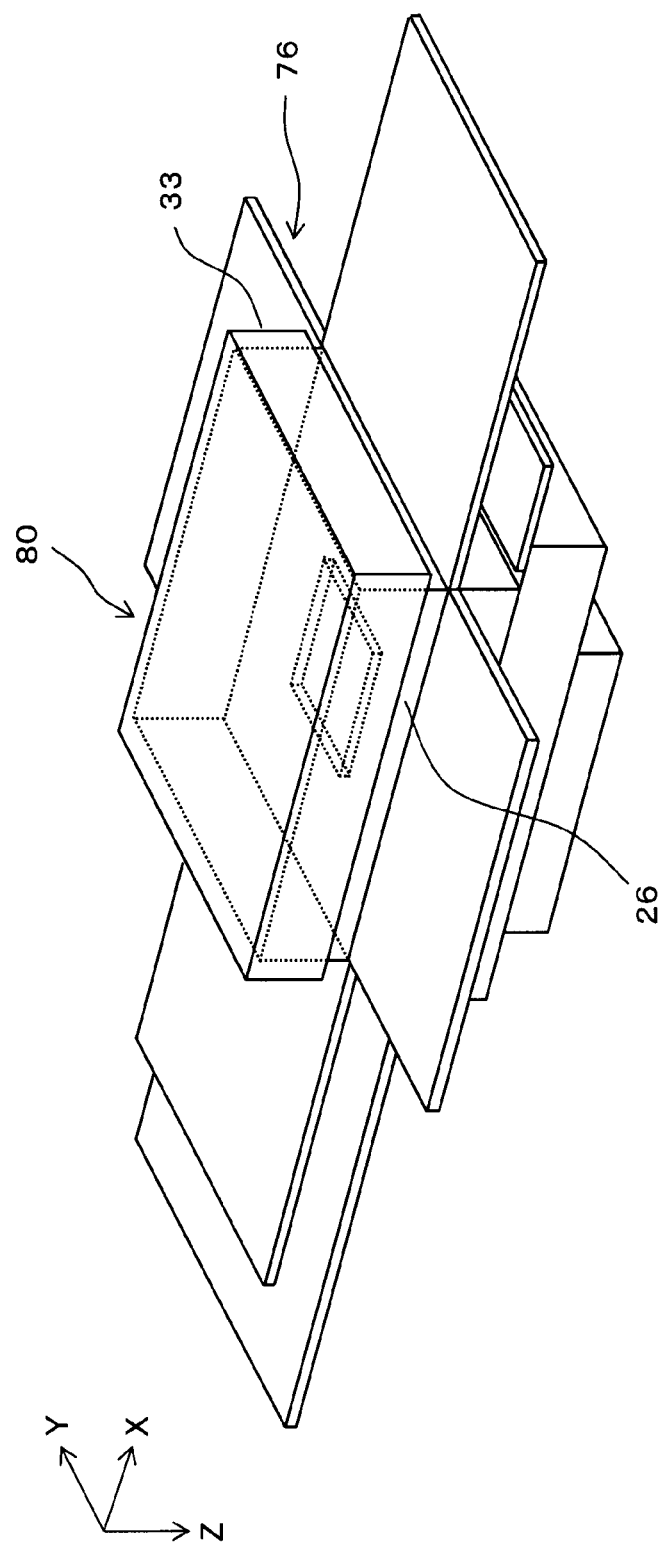
FIG. 8 is a diagram for explaining adhesion of a backing and a case.
Figure 9:
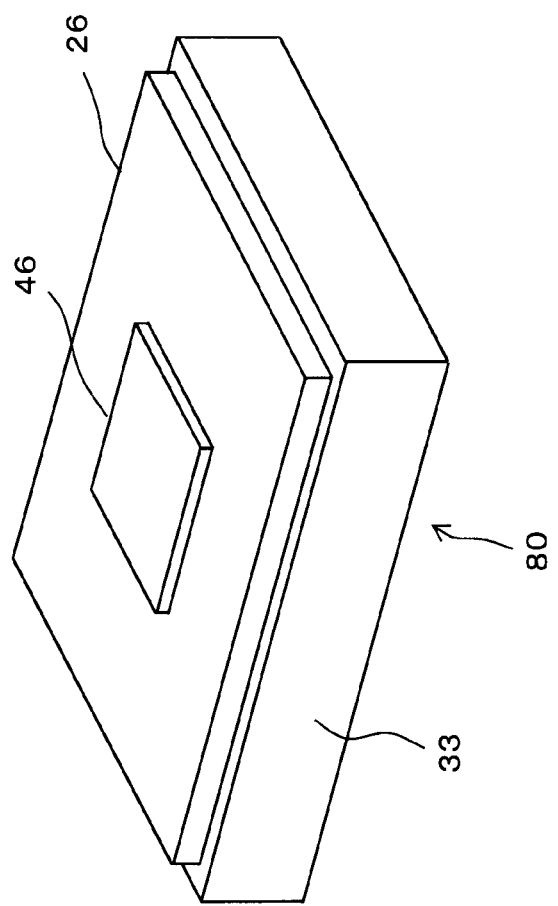
FIG. 9 is a diagram showing a protrusion provided on the backing.

In S14 of FIG. 6, the backing member and the backing case are adhered to the primary layered structure to which the heat dissipation sheet is adhered. Specifically, as shown in FIG. 8, a combined structure 80 is joined on the heat dissipation sheet 76. The combined structure 80 is formed from the backing member 26 and the backing case 33 housing the backing member 26. FIG. 9 shows a state where the combined structure 80 is placed upside down, and a projection 46 is formed on the center part on the living body side of the backing member 26. The combined structure is adhered on the heat dissipation sheet in such a manner that the projection 46 is fitted to the opening 78 shown in FIG. 7.

Figure 10:
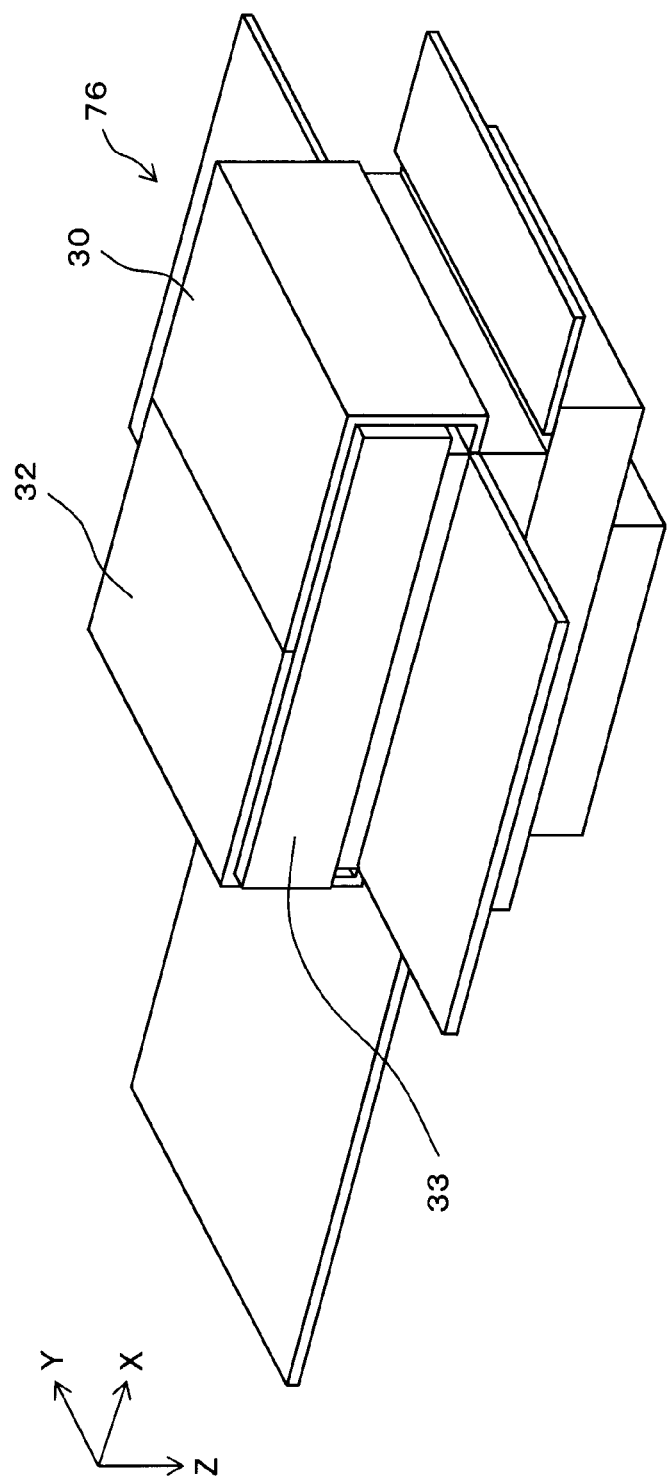
FIG. 10 is a diagram for explaining folding and adhesion of front and rear wings.

In S16 of FIG. 6, as shown in FIG. 10, the rear wing 30 and the front wing 32 are folded in the back surface side of the backing case 33; that is, the upper side in FIG. 10, and adhered and fixed. With this process, the backing case 33 and the heat discharge sheet 76 are integrated.

Figure 11:
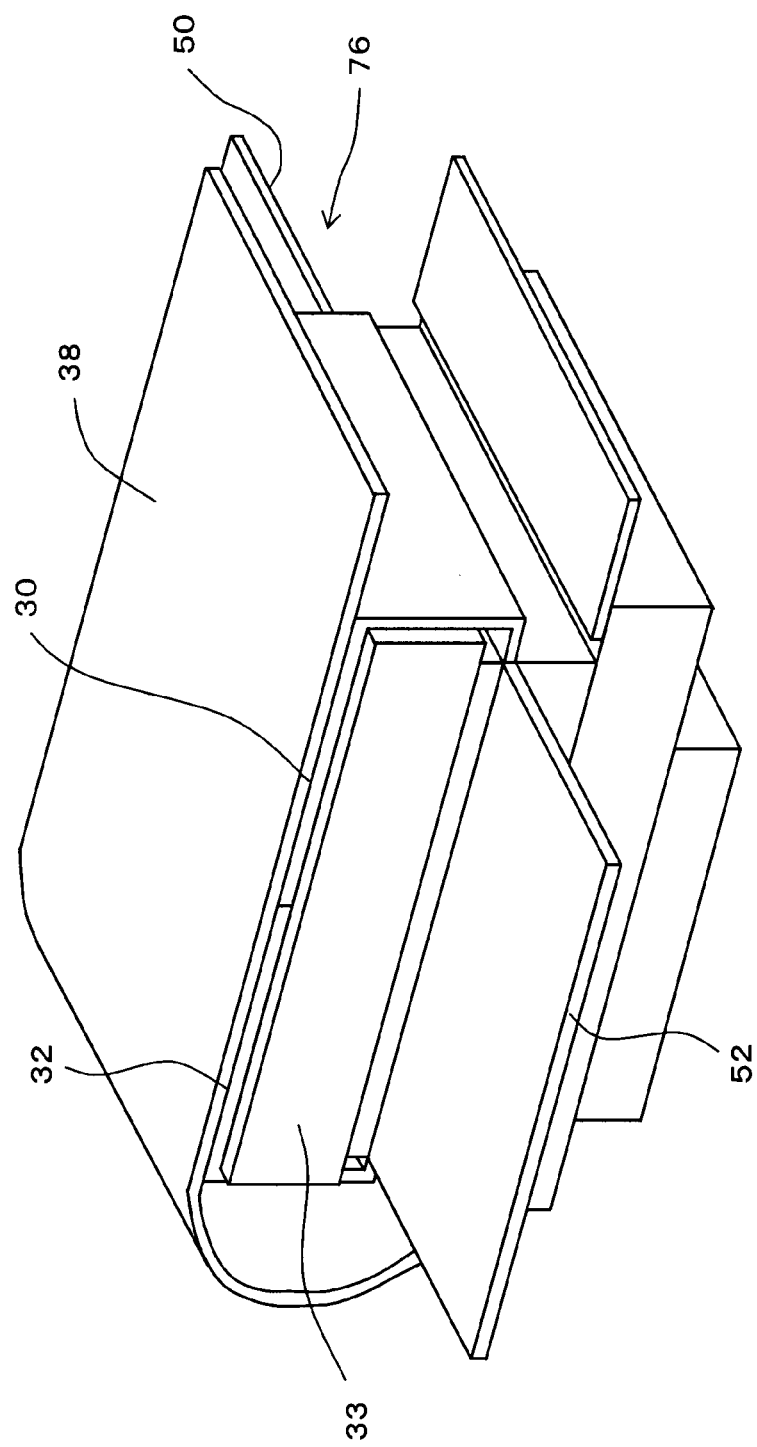
FIG. 11 is a diagram for explaining folding of a front side flexible board.

In S20 of FIG. 6, as shown in FIG. 11, the front side flexible board 38 is folded. Specifically, the front side flexible board 38 is folded to pass through the non-living body side of the backing case 33.

In S22 of FIG. 6, the assembly shown in FIG. 11 is placed in the heat discharge shell. Specifically, the heat discharge shell is assembled such that the backing case is sandwiched between two divided components, and, at the same time, the right wing and the left wing extend to the outside from the pair of the slits, and the inner assembly is placed within the heat discharge shell. In S24 of FIG. 6, the portions of the right wing and the left wing protruding from the slits are folded, and are adhered and fixed on the heat discharge shell. In S26 of FIG. 6, a wiring process, formation of the outer skin on the outer side of the heat discharge shell, and the like are executed, to form the probe as shown in FIG. 1.

As is clear from the above description, the rear wing and the front wing at the heat dissipation sheet achieve the fixation function of the backing case; that is, the backing member, and the right wing and the left wing at the heat dissipation sheet achieve a function to surround further from the outside the heat discharge shell which sandwiches the backing case. As a result of such multiple surrounding, the inner assembly is firmly fixed on the heat dissipation shell, and, at the same time, a reliable heat conduction route from the inner assembly to the heat discharge shell is constructed.

Figure 12:
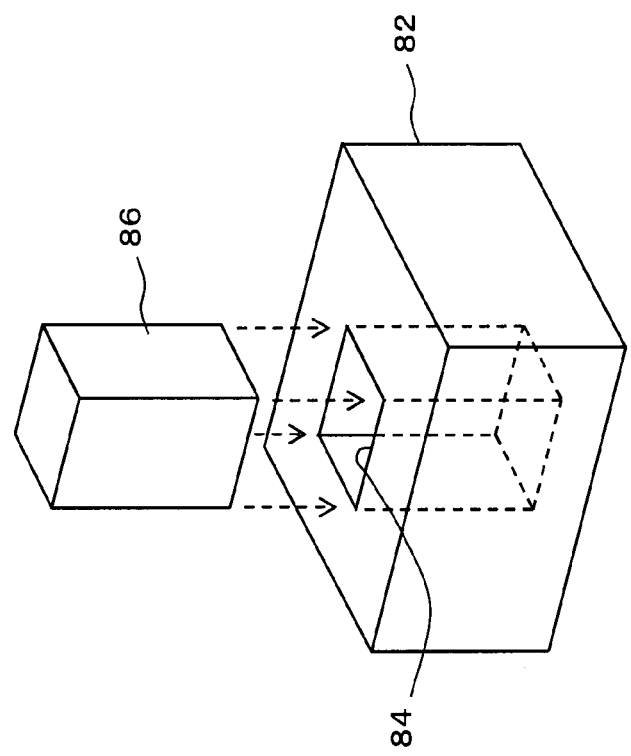
FIG. 12 is a diagram showing a backing and a heat dissipation member according to another preferred embodiment of the present invention.

FIG. 12 shows another preferred embodiment of the present invention. In the example configuration of FIG. 12, a heat dissipation member 82 is formed as a block-shaped member, and an opening 84 is formed at a center part thereof. A backing member 86 is inserted and fixed in the opening 84. This composite structure is joined to the back surface side of the electronic circuit board.

In such an embodiment also, the backing member 86 can be joined to the center part on the back surface side of the electronic circuit board; that is, a part where the ultrasound propagation most easily occurs, and, because the heat dissipation member 82 is joined at the periphery, sufficient heat absorption can be realized by the heat dissipation member 82. In other words, with such a configuration, both the absorption function of the ultrasound and the heat dissipation function can be achieved.

Figure 13:
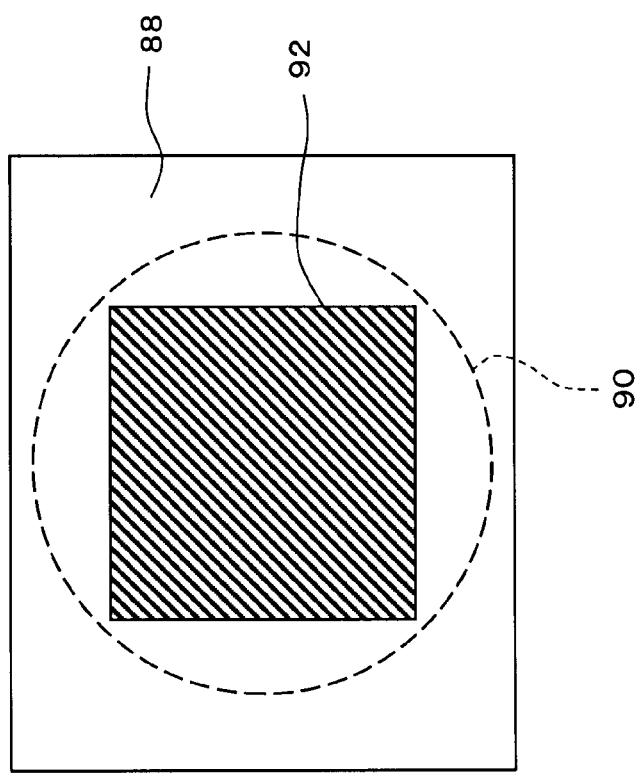
FIG. 13 is a diagram showing a relationship between a transmission/reception region and the backing member joining region.

FIG. 13 shows a two-dimensional region 88 corresponding to the array transducer. Reference numeral 90 shows an effective region actually used for transmission and reception, and is a circular region. In the setting of the region for joining the backing member, preferably, there is set a region having an area greater than or equal to 50 percent that of the entire region of the array transducer; specifically, the region at the center. In particular, as shown in FIG. 13, the backing region is preferably set as a region 92 which inscribes the effective region 90 actually used for transmission or reception or an equivalent region. According to such a configuration, the backing function may be achieved approximately uniformly over the entire array transducer.

The probe in the above-described embodiment is an esophagus probe, but the above-described structure may be applied to other body cavity insertion type probes, and also to probes other than the body cavity insertion type probe.

The invention claimed is:

1. An ultrasonic probe, comprising:
    an array transducer having a plurality of transducer elements which are arranged two-dimensionally;
    an electronic circuit board provided on a side of a back surface of the array transducer and having an electronic circuit which is electrically connected to the plurality of transducer elements; and a heat dissipation member which is a heat conductive member joined to a heat conductive region on a back surface of the electronic circuit board and which discharges heat from the back surface side of the electronic circuit board to a heat discharge structure, and wherein:

the heat conductive region and an ultrasound propagation region are set on the back surface of the electronic circuit board, the ultrasonic probe further comprises a backing member joined to the ultrasound propagation region, the ultrasound propagation region is a center region of the electronic circuit board, the heat conductive region is an entirety of or a part of a peripheral region of the electronic circuit board surrounding the center region, the heat dissipation member is a sheet-shaped member having an opening corresponding to the ultrasound propagation region, the backing member is a block-shaped member having a protrusion joined to the ultrasound propagation region through the opening, and the heat dissipation member is sandwiched between the electronic circuit board and the backing member.

2. The ultrasonic probe according to claim 1, wherein the heat dissipation member comprises a plurality of wings extending from the heat conductive region and having flexibility, and at least one wing of the plurality of wings is joined to the heat discharge structure.

3. The ultrasonic probe according to claim 2, wherein at least one slit is formed on the heat discharge structure, and the at lest one wing is inserted to the at least one slit, and an inserted portion of the at least one slit is folded and joined to an outer surface of the heat discharge structure.

4. The ultrasonic probe according to claim 2, further comprising:

a backing case that houses the backing member and that is formed by a heat conductive member, wherein at least one wing of the plurality of wings is folded and joined to the backing case, and the backing case is joined to the heat discharge structure.

5. The ultrasonic probe according to claim 1, wherein the heat dissipation member is a block-shaped member having an opening corresponding to the ultrasound propagation region, and the backing member is housed in the opening.

6. The ultrasonic probe according to claim 1, wherein the heat discharge structure is a heat conductive container that houses an inner assembly including the array transducer and the electronic circuit board.

7. The ultrasonic probe according to claim 6, wherein the heat conductive container is a probe head case that defines an outer shape of a probe head.

8. The ultrasonic probe according to claim 1, wherein the electronic circuit board is a semiconductor material board on a surface of which the electronic circuit is formed.

* * * * *